(12) United States Patent
Knes

(10) Patent No.: US 7,890,344 B2
(45) Date of Patent: Feb. 15, 2011

(54) METHOD FOR CREATING AN INDIVIDUAL SUPPLEMENT RECOMMENDATION

(76) Inventor: Otto Knes, Weierstrasse 18, Steckborn (CH) CH-8266

( * ) Notice: Subject to any disclaimer, the term of this patent is extended or adjusted under 35 U.S.C. 154(b) by 1410 days.

(21) Appl. No.: 11/078,602

(22) Filed: Mar. 11, 2005

(65) Prior Publication Data
US 2005/0240436 A1 Oct. 27, 2005

(30) Foreign Application Priority Data
Mar. 24, 2004 (CH) .................. 488/04

(51) Int. Cl.
G06Q 10/00 (2006.01)
G06Q 50/00 (2006.01)
(52) U.S. Cl. ........................................ 705/2
(58) Field of Classification Search ............ 705/2, 705/4
See application file for complete search history.

(56) References Cited

U.S. PATENT DOCUMENTS

2003/0110059 A1* 6/2003 Janas et al. ............. 705/2
2005/0177397 A1* 8/2005 Kane .................... 705/2

* cited by examiner

Primary Examiner—Gerald J. O'Connor
Assistant Examiner—John A Pauls
(74) Attorney, Agent, or Firm—Baker & Daniels LLP

(57) ABSTRACT

Disclosed herein is a method for creating an individual supplement recommendation for the targeted administration of certain micro nutrients in the human and animal organism determines the efficiency of the body's own antioxidative system is established by determining the effectiveness of at least one of three different body-own indicator groups, whereby, after the comparison of the actual value of the found indicators with the target value, it is determined whether or not the actual value still lies within a tolerable range of the target value and, in the case of the identification of an indicator that requires treatment, a database generates a corresponding supplement recommendation for the improvement of the indicator value via the allocation paths determined by the database.

7 Claims, 3 Drawing Sheets

Oxidative Stress

METHOD FOR CREATING AN INDIVIDUAL SUPPLEMENT RECOMMENDATION

Figure 1:
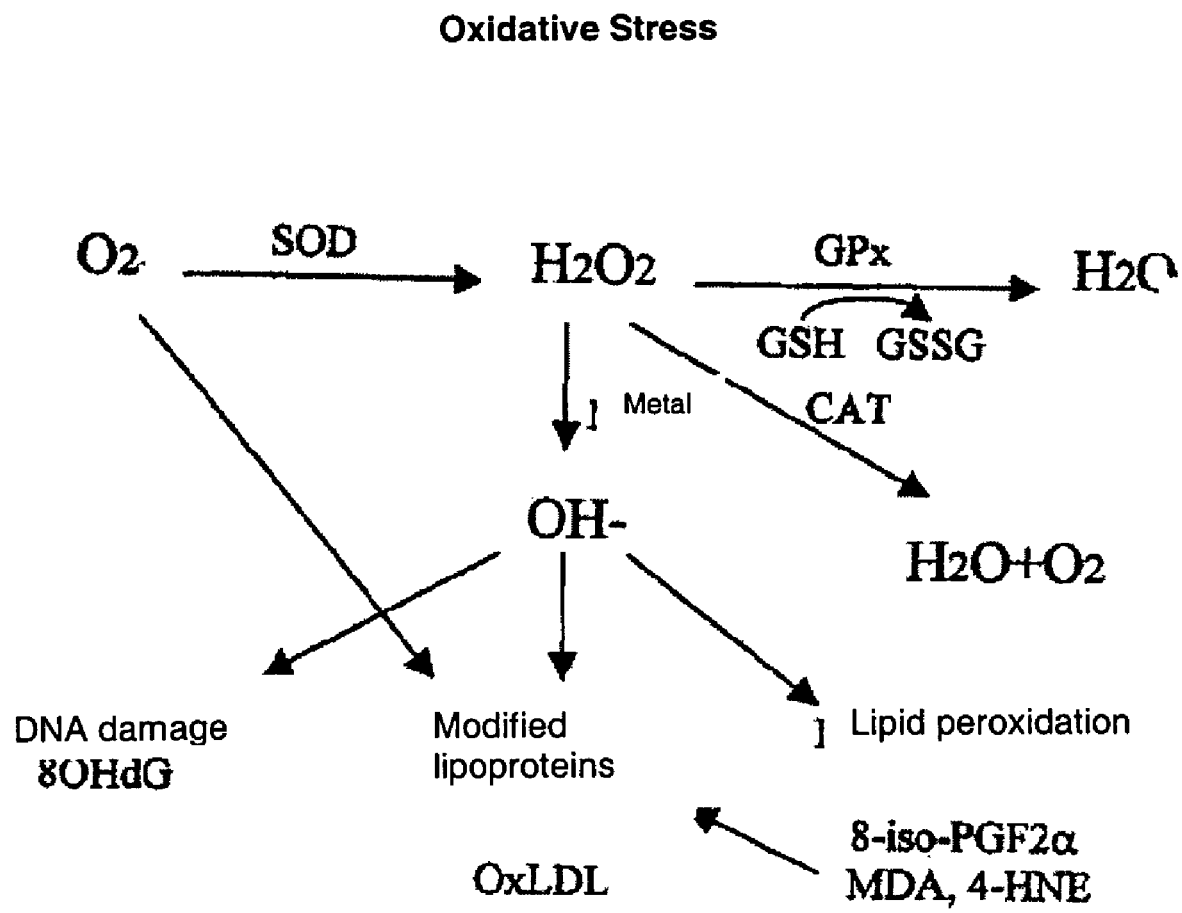

The invention relates to a method and a device for creating an individual supplement recommendation in accordance with the preamble of patent claim 1.

Dietary supplements are produced and marketed on a large scale with the goal of maintaining the health of the user and increasing his/her well-being. Thus, there are a number of combination preparations, in particular with added vitamin C, selenium, potassium, calcium, etc. to administer certain dietary supplements to the human or animal body. This dietary concept is solely based on the assumption that the human or animal organism to receive the supplement lacks certain substances that need to be compensated for by the addition of dietary supplements.

This type of administration of dietary supplements is unspecific and is associated with the risk that too many or the wrong dietary supplements will be taken.

Instead of the term "dietary supplement," the terms "micro nutrient" or "vital substance" are used as synonyms below.

The administration of these types of micro nutrients into the human or animal metabolism is accordingly unspecific and is not tailored to the special needs of the individual organism. In extreme cases, wrong or incorrectly dosed micro nutrients can damage the organism.

The term "oxidative stress" is understood to mean stress to the human or animal organism with, in particular, free radicals. Such free radicals are e.g. reactive oxygen compounds and other compounds that have a harmful effective in the cell, on the cell or on the cell membranes and other locations in the animal or human organism.

Oxidative stress has meanwhile been recognized and well documented scientifically as the cause or accelerator of many different diseases, including the aging process. However, the markers consulted for the characterization of the oxidative stress are inconsistent and no therapeutic consequence has yet been derived from the measurement values.

Certain molecules can become free radicals through metabolic processes or through environmental influences. These free radicals first react with oxygen to become very reactive oxygen compounds that can, in turn, react with sensitive body structures. This results in a damaged bio-molecule and thus another free radical that can continue the damaging effect.

The human or animal organism has systems that can detoxify such radicals to a certain extent. The body's own antioxidants as well as exogenous antioxidants have the task of supporting this radical detoxification. Depending on the cause and extent of the oxidative stress, different dosages and compositions of antioxidants are needed.

Thus, the object of the invention is to create a method and a device of the initially named type such that micro nutrients are provided and specially tailored for the respective individual so that the maximum efficiency of the body's own antioxidative systems can be utilized.

In order to solve the posed object, the invention is characterized by the technical doctrine in claim 1.

An important characteristic of the invention is that at least one of three different indicator groups are established to determine the efficiency of the body's own antioxidative systems.

A first group of indicators establishes the condition of the body's own detoxification system.

A second group of indicators establishes the quality of the body's own detoxification system, and a third group of indicators establishes the localization of the failure of the detoxification system.

Thus, with all three indicator groups, a comprehensive, individual conclusion on the oxidative stress of the human or animal organism is provided for at different locations in the organism.

However, the invention is not inevitably limited to the AND linking of the three indicator groups.

In a further embodiment of the invention, it is provided that only two or more indicator groups in any combination lead to the technical doctrine according to the invention.

The first indicator group concerns the determination of the state of the detoxification system. Such a determination is important because this detoxification system represents a first line of defense against an attack with oxidative radicals. For this reason, it is advisable and necessary to first establish the state of the body's own detoxification system of an organism.

The second indicator group concerns the determination of the quality of the body's own detoxification system. With the determination of this performance, the ability of the organism to deal with oxidative stress can be determined. This indicator group determines the ability of the human or animal organism to defend itself against oxidative stress.

With the third indicator group, individual spots where the body's own detoxification system may break down are now localized in the organism. This type of breakdown spot can e.g. be the extent of the damage to a cell membrane or the damage to lipoproteins or damage to DNA.

As a result, with the aforementioned three indicator groups, functional tests are performed on the organism that lead to conclusions regarding the state of the detoxification system, the quality of the detoxification system, and the failure of the detoxification system. Thus, an important difference is reached compared to the state of the art, since, in the state of the art, micro nutrients were added unspecifically and without regard for the function of the organism and its ability to defend itself against oxidative stress. It was simply assumed that this and any micro nutrients have a positive effect on the organism.

The invention extends far beyond this thought process, then the invention now suggests a method for creating an individual supplement recommendation (supply of micro nutrients) that is geared towards one or more of the aforementioned indicator groups.

As a result of the specific functional tests with the three aforementioned indicator groups, the invention can reach a conclusion on a necessary supply of micro nutrients.

This has the advantage that an extensive functional analysis is first performed on the organism with respect to oxidative stress in order to then—based on this analysis—add certain micro nutrients specifically and individually.

The supply of the wrong micro nutrients or too high a dosage of micro nutrients is thus avoided.

Incidentally, it is possible to limit oneself to the administration of micro nutrients that were determined to be lacking in the performed functional tests. Thus, excess or even harmful micro nutrients are not administered.

The indicators are assigned to the micro nutrients as follows:

Determination of the Overall Antioxidative Capacity in the Plasma

This mainly reflects the water-soluble antioxidants like vitamin C, glutathione, as well as the body's own antioxidative substances like uric acid, bilirubin, etc. An antioxidative capacity that is too low will be counteracted by water-insoluble antioxidants like vitamin C.

Determination of the Intracellular Concentration of Reduced Glutathione or the Ratio of Reduced to Oxidized Glutathione Reduced glutathione (GSH) is the most important intracellular antioxidant. Cell functions rise and fall based on its availability. New insight also shows the interconnection between the redox potential in the cell (controlled by the ratio of oxidized to reduced glutathione) and the realization of inflammation reactions, determined by nuclear factors, mainly NFkappaB. A glutathione concentration that is too low can be increased through the supplementation of precursor substances like N-acetylcystein or special forms of glutathione. Certain proteins (e.g. whey) or substances with low redox potentials, such as alpha lipoic acid, also increase GSH.

Activity of the Superoxide Dismutase (SOD) Enzyme

Cofactors of SOD are zinc, manganese, and copper. These substances are added in the event of abased activity values. Increased values can be caused by heavy metal stress or oxidative stress (induction).

Activity of the Glutathione Peroxidase (GPx) Enzyme

The cofactor of this enzyme is selenium, which is added according to activity level of the supplementation.

Activity of the Catalase (CAT) Enzyme

The cofactor of this enzyme is iron, which is added according to the activity level of the supplementation.

8-isoprostane, Malondialdehyde, or 4-hydroxyalkenals

The levels of function of these markers is established for the Determination of the Extent of the Damage to the Cell Membrane.

Oxidized Form of the LDL-cholesterol (oxLDL) for the Determination of the Degree of Damage of Lipoproteins With the last three damage indicators named, damage to the unsaturated fatty acid on membranes or other sensitive biomolecules is meant. By administering high doses of tocopherole (vitamin E derivative), they are built into the membrane and improve oxidation resistance there.

Through different individual metabolistic functionalities, explainable through genetic diversities (polymorphisms, mutations) or the different expression regulations of the proteins in the genes, the need for vital substances is different for each individual. Even the different exposition with respect to environmental or social influences makes individual treatment necessary. The determination of these functional differences enables the assignment of individual vital substances for an individual supplement strategy.

The already described markers of oxidative stress can be enhanced by other indicators relevant for the balance of vital substances for a more exact modification of the supplement recommendation. Examples of this are:

Homocystein for the determination of the dosage of the vitamins folic acid, vitamin B6, and vitamin B12

CRP ultra-sensitive for the identification of inflammation processes and corresponding use of anti-inflammatory substances like omega-3 fatty acids Blood lipids for estimating the cardiovascular risk The combination of the aforementioned markers allows the detailed identification of malfunctions in the radical metabolism and thus the described, targeted and individual measures.

It is also pointed out once again that any combination of the aforementioned indicators is also sufficient to determine the oxidative stress of the organism and to use corresponding countermeasures by adding micro nutrients.

As a result of the aforementioned functional tests, all determined indicators are now imported into a database and then compared with target values saved there. The target values were obtained from medical literature and establish a specific normal range of the indicator, outside of which an undesired deviation is determined.

After comparing the actual value of the found indicator with the target value, the next step is to determine whether or not the actual value still lies within the tolerable range of the target-value.

According to this decision, it must now be decided whether or not the found indicator needs to be treated.

If it is decided that the indicator requires treatment, an appropriate micro nutrient is sought to improve this indicator value and it is added to a supplement recommendation as a combination substance.

Examples of the Composition of Supplement Recommendations

EXAMPLE 1

| Analysis Data: | |
|---|---|
| Antioxidative capacity: | In target range |
| SOD | Slightly low activity |
| GPx | Slightly low activity |
| GSH | In target range |
| Damage marker | In target range |
| Homocystein | Slightly elevated |
| Supplementation: | |
| Zinc: | 15-20 mg/d |
| Copper: | 2-4 mg/d |
| Manganese: | 5-10 mg/d |
| Selenium: | 50-150 mg/d |
| Folic acid: | 0.8 to 1 mg/d |
| Vitamin B6: | 20-40 mg/d |
| Vitamin B12: | 30-100 mcg/d |

The exact recommendations still depend on body weight, sex, and age.

EXAMPLE 2

| Analysis Data: | |
|---|---|
| Antioxidative capacity: | In target range |
| SOD | Slightly low activity |
| GPx | Obviously low activity |
| GSH | Too low |
| Damage marker | 8-iso PGF2 elevated |
| Homocystein | Greatly elevated |
| CRP | Slightly elevated |
| Supplementation: | |
| Zinc: | 15-20 mg/d |
| Copper: | 2-4 mg/d |
| Manganese: | 5-10 mg/d |
| Selenium: | 100-200 mg/d |
| Folic acid: | 1 to 1.6 mg/d |
| Vitamin B6: | 40-60 mg/d |
| Vitamin B12: | 200-400 mcg/d |
| N-acetylcystein: | 150-300 mg/d |
| Alpha lipoic acid: | 100-200 mg/d |
| Tocopherole: | 400-600 mg/d |
| Vitamin C: | 750-1500 mg/d |
| Omega-3 fatty acids: | 0.8-1.2 g/d |

The exact recommendations still depend on body weight, sex, and age.

The function of the individual micro nutrients will now be explained in greater detail based on example 2.

The three substances zinc, copper and manganese are activators of SOD and improve the activity of the SOD enzyme.

Selenium causes an improvement in the enzyme activity of the GPx enzyme. Folic acid, vitamin B6, and vitamin B12 participate in the decomposition of homocystein and lead to a drop in the homocystein level in the organism.

The N-acetylcystein is a precursor of the reduced glutathione (GSH) and improves its intracellular synthesis.

The addition of alpha lipoic acid also improves the synthesis of the GSH.

The tocopherole together with vitamin C protect the cell membrane from oxidative damage and the omega-3 fatty acids counteract the inflammatory reactions.

The object of this invention not only results from the object of the individual patent claims, but also from the combination of the individual patent claims.

All data and characteristics disclosed in the documents, including the summary, in particular the spatial formation in the drawings, are claimed as important to the invention provided that they are new individually or in combination compared to the state of the art.

The invention is explained in greater detail below using drawings only representing one embodiment. Additional characteristics and advantages of the invention emerge from the drawings and their description.

They show:

FIG. 1: Interconnectedness of individual markers during radical detoxification

Figure 2:
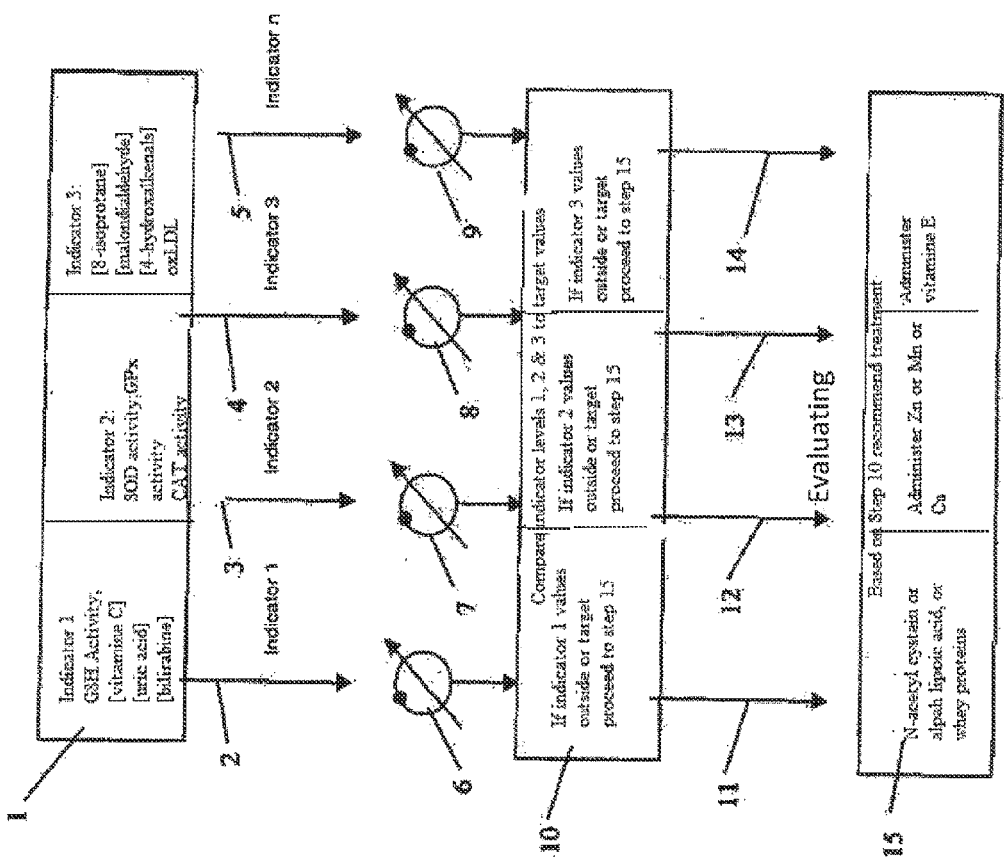
Figure 3:
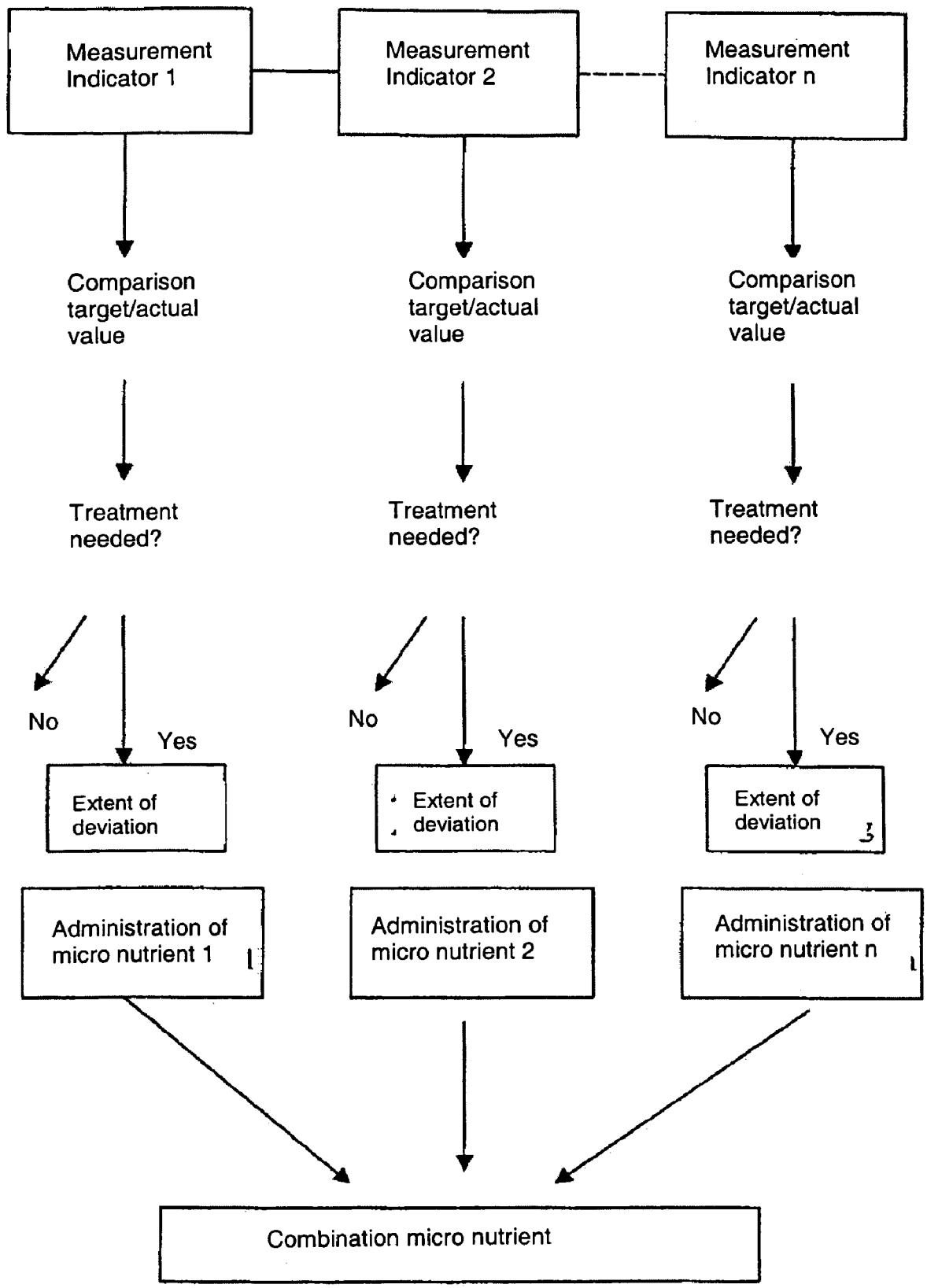

FIG. 2: Schematized representation of a device for creating an individual supplement recommendation;

FIG. 3: Schematizes the decision tree for the measurement device according to FIG 2.

Considering the diagram in FIG. 1, the interconnectedness of the individual markers can be recognized during radical detoxification. The function of the markers specified there was described above.

In accordance with FIG. 2, their measurement values are captured in a measurement device 1 for determining the value of the indicators. The measurement procedures for determining the size of each indicator are not described further here.

As an example for this type of known measurement method, the determination of the antioxidative capacity in the plasma is explained as follows:

A colorless pigment is added to the plasma. This substance takes on a blue color in the presence of radicals because it reacts with radicals.

A radical generator is also added to the plasma. At a certain time, the production of radicals is started by the radical generator. The created radicals are first caught by the blood plasma and can thus not react with the colorless pigment ABDS. Only when the capacity of the plasma to accept radicals is exhausted do they react with the ABDS pigment and thus cause a blue coloring of the solution. The time when the blue coloring of the plasma begins is a measure for the ability of the plasma to intercept free radicals.

This measurement procedure is only used as an example for the inherently known measurement procedures for determining the other indicators as well.

Indicators 1, 2, 3 through n are thus determined in the named measurement device 1. The measurement results are read out via the measurement flags 2-5 and imported into a target/actual value comparer 6-9.

There, the separation distance between the target value and the actual value of the respective indicator is determined and this distance is imported into a database 10.

Decision-making processes take place in database 10 to determine whether or not the distance between the target and the actual value of each indicator requires treatment. If it is determined to require treatment, the database generates an appropriate supplement recommendation via the allocation paths from the database to improve the indicator value. These allocations 11-14 are imported into a supplement recommendation and a combination micro nutrient preparation is created from this.

The decision-making processes running in the measurement device in accordance with FIG. 2 are roughly schematized again based on FIG. 3. It can be recognized there that the addition of a corresponding micro nutrient 1 . . . n only takes place at a certain level of deviation between the target value and the actual value of the respective indicator. Thus, a combination micro nutrient is then created from all micro nutrients.

It is important for the invention that a number of indicators are established with functional tests for the determination of the oxidative stress in the organism at different points of the metabolism. Only through this determination of the indicators at different points of the metabolism can the oxidative stress be determined and influences at the different points in the metabolism. Thus, a completely new approach is achieved for the creation of a combination micro nutrient tailored to individual circumstances.

Only by obtaining indicators at different spots in the organism is it possible to determine the oxidative stress created there and, as a consequence thereof, achieve an individual adaptation of a combination micro nutrient.

The invention concerns a novel, individual formation of a vital substance supplementation.

DRAWING LEGEND 1 measurement device
2 measurement path
3 measurement path
4 measurement path
5 measurement path
6 target/actual value comparer
7 target/actual value comparer
8 target/actual value comparer
9 target/actual value comparer
10 database
11 allocation
12 allocation
13 allocation
14 allocation
15 recommendation

The invention claimed is:

1. A system for creating an individual supplement recommendation for targeted administration of certain micro nutrients in the human and animal organism, said system characterized in that efficiency of the body's own antioxidative system is established by determining the effectiveness of at least one of three different body-own indicator groups, said system comprising at least one measurement device: wherein the at least one device measures:

a first group of indicators that determines the state of the body's own detoxification system, wherein said first group of indicators includes at least one indicator selected from the group consisting of reduced glutathione (GSH), vitamin C, uric acid, and bilirubin, a second group of indicators that determines the quality of the body's own detoxification system wherein said second group of indicators includes at least one indicator selected from the group consisting of SOD, GPx and catalase enzyme (CAT), and a third group of indicators that determines the location of the failure of the detoxification system wherein said third group of indicators includes at least one indicator selected from the group consisting of: 8-isopentane, malondildhyde, 4-hydroxyalkenals and ox LDL wherein functional tests are performed on the organism that lead to conclusions with respect to the state of the detoxification system, the quality of the detoxification system, and the localization in the event of the failure of the detoxification system;

said device further characterized in that activity of the enzyme superoxide dismutase (SOD) is determined, activity of the enzyme glutathione peroxidase (GPx) is determined, function of a marker selected from the group consisting of 8-isoprostane, malonedialdehyde, and 4-hydroxy-alkenals is established for the determination of the extent of the damage to the cell membrane; and the oxidized form of the LDL-cholesterol (oxLDL) is established for the determination of the extent of the level of damage to the lipoproteins;

wherein measurement values of the indicators are captured in a measurement device (1);

indicators (1, 2, 3) are determined in the measurement device (1) and the measurement results are read out via a measurement flag (2-5) and imported into a target/actual value comparer (6-9);

distance between the target value and the actual value of each indicator is determined and imported into a database (10), in which a decision-making process takes place to determine whether or not the distance between the target and the actual value of the respective indicator requires treatment; and in the case of the identification of an indicator that requires treatment, the database generates a corresponding supplement recommendation for the improvement of the indicator value via the allocation paths determined by the database.

2. The system of claim 1, characterized in that the overall antioxidative capacity in the plasma is determined.

3. The system claim 1, characterized in that a determination of the intracellular concentration of reduced glutathione takes place.

4. The system of claim 1, characterized in that a determination of the ratio of reduced to oxidized glutathione takes place.

5. The system of claim 1, characterized in that the activity of the enzyme catalase (CAT) is determined.

6. The system of claim 1, characterized in that the function of 8-OH-deoxyguanosin (8OHdG) is established for the determination of the extent of the oxidative damage to the DNA.

7. The system of claim 1, characterized in that one or more of the results of the functional tests with the determined indicators are imported into a database and then compared with the target values saved there.

* * * * *